United States Patent [19]

Campbell

[11] Patent Number: 5,447,947

[45] Date of Patent: Sep. 5, 1995

[54] COMPOSITIONS AND METHODS OF TREATMENT OF SYMPATHETICALLY MAINTAINED PAIN

[75] Inventor: James N. Campbell, Lutherville, Md.

[73] Assignee: ARC 1, Lutherville, Md.

[21] Appl. No.: 905,496

[22] Filed: Jun. 25, 1992

Related U.S. Application Data

[63] Continuation of Ser. No. 661,554, Feb. 26, 1991, abandoned, which is a continuation-in-part of Ser. No. 485,156, Feb. 26, 1990, Pat. No. 5,070,084.

[51] Int. Cl.$^6$ ............................................. A61K 31/415
[52] U.S. Cl. ..................................... 514/392; 424/449
[58] Field of Search ................. 424/449, 448; 514/392

[56] References Cited

U.S. PATENT DOCUMENTS

| | | | |
|---|---|---|---|
| 4,201,211 | 5/1990 | Chandrasekaran et al. | 424/443 |
| 4,250,191 | 2/1981 | Edwards | 424/308 |
| 4,310,535 | 1/1982 | Pierpaoli | 424/273 |
| 4,443,441 | 4/1984 | Galin | 424/244 |
| 4,742,054 | 5/1988 | Naftchi | 424/468 |
| 4,801,587 | 1/1989 | Voss et al. | 514/248 |

OTHER PUBLICATIONS

Raynayd's Phenomenon and Disease Merck Manual Holvey, Ed. 1972, p. 487.
CA 108:124399 Nakamura et al in Eur, J. Pharmacol (1988) 146 (2-3), 223-8.
CA:107:51700 Ito et al. in Jpn. J. Pharmacol. (1987) 44 (2) 121-6.
Curtis and Marwah, "Evidence for Alpha Andrenoceptor Modulation of the Nociceptive Jaw-Opening Reflex in Rats and Rabbits" J. Pharmacology Experimental Therapeutics 238, 576-579 (Aug. 1988).
Sagen and Proudfit, "Evidence for Pain Modulation by Pre- and Postsynaptic Noradrenergic Receptors in the Medulla Oblongate" Brain Research 331, 285-293 (1985).
M. Ishizuki, Letter to the Editor, "Clinical Application of Guanethidine Ointment to the Treatment of Painful States and Allodynia" Clinical Journal of Pain 261 (1988).
Janig, W., Trends in NeuroSciences 8(11), 471-77 (1985).
Loh, L., et al., J. Neurol. Neurosurg. Psychiat. 41(7), 664-71 (1978).
Naftchi, N., Chem. Abst. 110(9):69410r.
Nakagawa, et al., Chem. Abstr. 111(2):12526z.
Nakagawa, et al., Chem. Abstr. 110(12):101838z.
Gonzales, et al., J. Neurochem. 53(5), 1595-98 (1989).
Hobelmann, et al., Microsurg. 10(2), 151-53 (1989).
Price, et al. Pain 36(3), 273-88 (1989).

Primary Examiner—Thurman K. Page
Assistant Examiner—Neil Levy
Attorney, Agent, or Firm—Patrea L. Pabst

[57] ABSTRACT

Sympathetically maintained pain is treated topically by administering to the site where sympathetically maintained pain is present an α-adrenergic antagonist, α-1-adrenergic antagonist, α2 adrenergic agonist, or other drug that depletes or blocks synthesis of sympathetic norepinephrine. Examples demonstrate relief of pain by application of phentolamine or clonidine.

5 Claims, No Drawings

COMPOSITIONS AND METHODS OF TREATMENT OF SYMPATHETICALLY MAINTAINED PAIN

This is a continuation of application Ser. No. 07/661,554 filed on Feb. 26, 1991, abandoned which is a continuation-in-part of U.S. Ser. No. 07/485,156 entitled "Diagnosis and Treatment of Sympathetically Maintained Pain" filed Feb. 26, 1990 by James N. Campbell, now U.S. Pat. No. 5,070,084.

BACKGROUND OF THE INVENTION

The invention relates to the diagnosis and treatment of sympathetically maintained pain using compounds blocking the action of norepinephrine at the alpha adrenergic receptors.

Several chronic, non-malignant pain syndromes such as causalgia and reflex sympathetic dystrophy have one feature in common: blockade of the sympathetic innervation of the affected body region can lead to pain relief. The pain may result from skeletal, soft tissue, or nerve injury. Terms such as reflex sympathetic dystrophy, Sudek's atrophy, and causalgia have all been used to refer to such patients. The term "sympathetically maintained pain" ("SMP") encompasses all pain syndromes that can be relieved by sympathetic blockade.

Patients with SMP typically have both stimulus-independent (ongoing) pain and stimulus-dependent pain (hyperalgesia). Hyperalgesia is defined as a leftward shift of the stimulus-response function, such that a lowering of pain threshold and/or an increase in pain to suprathreshold stimuli is observed. The decrease in pain threshold to mechanical stimuli may be such that lightly stroking the skin evokes pain, a phenomenon sometimes referred to as allodynia.

Conventional treatments for SMP include repeated local anesthetic sympathetic blocks, intravenous regional guanethidine/reserpine blocks, surgical sympathectomy, or oral sympatholytic therapy. However, each of these treatments carries with it a degree of risk, side effects and discomfort.

One method of diagnosis of SMP is by assessment of the results of a local anesthetic blockade of the sympathetic ganglia (LABSG) that innervate the painful part. Because of the technical expertise required in the performance of the LABSG and the potential complications associated with the LASB, alternate tests for the diagnosis of SMP have been studied. For example, intravenous regional blockage (IVRB) of sympathetic function with guanethidine has been used as a means for the diagnosis and treatment of SMP.

There are several potential disadvantages to the use of LABSG and IVRB. LABSG is subject to false negative results if the local anesthetic fails to anesthetize adequately the sympathetic ganglia. The anesthetic may reach the somatic afferents in the nearby nerve roots and produce pain relief because of concurrent somatic blockade, and certain afferents may in addition course with sympathetic efferents. Certain patients tolerate poorly the application of the tourniquet required with IVRB. LABSG involves strategic localization of the needle prior to injection, and thus fluoroscopy is often needed. With IVRB, the guanethidine may escape into the systemic circulation with resultant systemic untoward effects. A series of complications have been reported with LABSG, including pneumothorax, injury to the kidney, inadvertent systemic application, spinal anesthesia, hemorrhage, etc. It is difficult to evaluate placebo responses with both LABSG and IVRB.

It would therefore be advantageous to have a method of diagnosis and treatment that does not exhibit these difficulties.

Several lines of evidence suggest that peripheral adrenergic receptors are involved in SMP. Stimulation of the peripheral but not central cut end of the sympathetic chain reproduces pain in causalgia patients after sympathectomy. Local anesthetic blockade of the appropriate sympathetic ganglion or adrenergic blockade via intravenous administration of phentolamine, rapidly abolishes sympathetically-maintained pain and hyperalgesia. Depletion of peripheral catecholamines by regional intravenous guanethidine relieves pain and hyperalgesia. Intradermal injection of norepinephrine rekindles the pain and hyperalgesia that had been relieved in patients by sympathectomy or sympathetic block but does not cause pain or hyperalgesia in normal subjects. The non-specific α-adrenergic antagonist phenoxybenzamine and the specific $\alpha_1$-adrenergic antagonist prazosin can be effective in relieving pain in patients with SMP. The beta-adrenergic antagonist propranolol has little effect on SMP.

It is therefore possible that administration of an α-adrenergic blocking agent could be beneficial in the treatment of SMP patients. Therapeutic uses of the α-adrenergic compounds, for example, phentolamine and clonidine, are known in the art. For example, U.S. Pat. No. 4,801,587 discloses the use of phentolamine as a vasodilator to treat impotence. U.S. Pat. No. 4,310,535 discloses the use of phentolamine in combination with other drugs for use in the control of immune reactions. The use of phentolamine and clonidine for controlling hypertension is disclosed in U.S. Pat. No. 4,250,191. α-Adrenergic drugs have been found to be useful in the stabilization of intraocular lenses, as disclosed in U.S. Pat. No. 4,443,441. U.S. Pat. No. 4,201,211, discloses the use of a clonidine patch for therapeutic use as a stimulant for the central nervous system.

It is therefore an object of the present invention to provide a topical method of diagnosis for sympathetically maintained pain that has a low incidence of false positives and false negatives.

It is another object of the present invention to provide a topical method of diagnosis and treatment of sympathetically maintained pain that has a low incidence of adverse reactions with relatively minor complications.

SUMMARY OF THE INVENTION

Sympathetically maintained pain is treated topically by administering to the site where sympathetically maintained pain is present an α-adrenergic antagonist, $\alpha_1$-adrenergic antagonist, $\alpha_2$ adrenergic agonist, or other drug that depletes or blocks synthesis of norepinephrine from the sympathetic terminals.

Examples demonstrate relief of pain by application of phentolamine or clonidine.

DETAILED DESCRIPTION OF THE INVENTION

Sympathetic efferent fibers release norepinephrine which in turn activates α-adrenergic receptors. Activation of the α-adrenergic receptors by norepinephrine, either directly or indirectly, excites nociceptors. Activity in the nociceptors then evokes pain and further activity in the sympathetic efferent fibers. This, in turn, results in further discharge of the nociceptors. The goal in therapy is to block the effects of norepinephrine on nociceptors. Topical application to the site where sympathetically maintained pain is present of an α-adrenergic antagonist, $α_1$-adrenergic antagonist, $α_2$ adrenergic agonist, or other drug that depletes or blocks synthesis of norepinephrine at the sympathetic terminals (collectively referred to herein as "adrenergic neuron blocking agents") relieves the pain.

These compounds are known to those skilled in the art. For example, the various classes of compounds and examples thereof are described in *The Pharmacological Basis of Therapeutics*, 8th Edition, Gill, A. G., T. W. Rall, A. S. Nies, P. Taylor, editors (Pergamon Press, Co., Inc., NY 1990), the teachings of which are incorporated herein.

α-adrenergic Blocking Agents

α-adrenergic blocking agents bind selectively to the α class of adrenergic receptors and thereby interfere with the capacity of sympathomimetic amines to initiate actions at these sites. α-Adrenergic blockade is due to the direct action of these drugs on α receptors and is independent of any effects on adrenergic neurons or on the basic response mechanisms of effector cells. β-Adrenergic receptors are not affected by conventional doses of any α-blocking agent currently in use.

Examples of α-adrenergic antagonists include phenoxybenzamine, dibenzamine, phentolamine, tolazoline, and prazosin. Phenoxybenzamine and dibenzamine bind covalently to the α receptor and produce an irreversible type of blockade. Phentolamine, tolazoline, and prazosin bind reversibly and antagonize the actions of sympathomimetic amines competitively. There are differences in the relative abilities of α-adrenergic blocking agents to antagonize the effects of sympathomimetic amines at the two subtypes of α receptors, $α_1$ and $α_2$ receptors. Phenoxybenzamine is approximately 100-fold more potent in blocking $α_1$ (postsynaptic) receptors than $α_2$ receptors (that modulate neural release of transmitter). Prazosin is also a highly selective $α_1$-blocking agent, while phentolamine is only three to five times more potent in inhibiting $α_1$- than $α_2$-adrenergic receptors. In contrast, yohimbine is a selective $α_2$ blocker and has been shown to prevent the antihypertensive effect of systemic clonidine. Phentolamine is the preferred α-adrenergic antagonist at this time.

These compounds have previously been administered systemically, either orally or by injection. Systemic administration requires high doses and thus systemic side effects (e.g., postural hypotension, tachycardia, nasal stuffiness, headache) limit their usefulness. In the method described herein, the compounds are administered topically, in a suitable pharmaceutical carrier, many of which are known to those skilled in the art. The carrier can be in the form of a lotion, ointment, solution, or transdermal patch. The topical application allos the drug to reach high concentration at the desired target without apprciable systemic dosing. Thus the many of the side effects of these compounds, observed following systemic administration, are avoided by topical administration.

Another drug class, $α_2$-agonists, the preferred example being clonidine, an antihypertensive agent stimulating both central and peripheral $α_1$- and $α_2$-adrenergic receptors, also antagonize the effects of norepinephrine. This is because sympathetic terminals possess $α_2$-receptors which when activated block the release of norepinephrine. Thus the $α_2$-agonists such as clonidine antagonize $α_1$-receptors indirectly by preventing the release of norepinephrine.

A third class of effective drugs are those that deplete norepinephrine from the sympathetic terminals. The prototype drug in this class is guanethidine. Other examples are bretylium, bethanidine, debrisoquin, and reserpine.

Additional compounds are specific inhibitors of catecholamine synthesis and monoamine oxidase inhibitors.

These compounds are normally administered systemically (orally or by intravenous injection), although as described herein they are administered in a pharmaceutically acceptable topical carrier, as described above.

The effective dosage of these compounds is determined by applying dosages of the compound to the affected site and observing local vasodilatation. Vasodilatation can be determined by laser Doppler flow measurements or by measuring local increases in skin temperature.

EXAMPLE 1

Demonstration of Effectiveness of Intravenous Administration of Blocking Agent

If peripheral α-adrenergic receptors are blocked completely, skin temperature would approach core temperature. Such a blockage would produce profound hypotension and a reflex tachycardia. Therefore, a cumulative dose of phentolamine was selected such that the heart rate did not exceed 150 beats per minute and the effects on blood pressure were mild. This dose ranged from 35 mg to 45 mg over a 30 minute period. Preliminary studies suggested that this amount of phentolamine effectively relieved pain in patients with SMP.

The heart rate, systolic and diastolic blood pressure changes produced by phentolamine in a typical patient were relatively mild. In the first seven patients phentolamine alone was administered. The heart rate increased moderately. In subsequent sessions, patients pretreated with propranolol 1-2 mg showed minimal increase in pulse rate. Blood pressure was little effected regardless of whether propranolol was given as patients were maintained in a supine position.

One patient, an 18 year old woman, was treated for severe pain in the right foot. The patient had a thorough examination but no clear initiating cause of the pain was determined. The patient was disabled and could not walk due to the severity of the pain. A thorough neurological exam disclosed a restricted zone of hyperalgesia on the plantar surface of the foot that was consistent over several examinations. No psychiatric problems were present in an otherwise normal productive college student performing well in school.

The patient was diagnosed as having SMP and then underwent local LABSG, and the administration of phentolamine systemically by intravenous injection.

Placebo trials indicated that patient showed no change in pain when normal saline was injected IV.

Phentolamine given IV with an accumulated dose of 25 mg over 15 minutes led to an 80% reduction in pain as measured by visual analysis scores and LABSG led to 50% relief of pain in a separate study.

Ratings of stimulus-independent pain did not change for 10 minutes following the initial phentolamine administration. The first 4 boli of phentolamine (total dose=15 mg) resulted in a gradual decrease in pain of about 50%. After two further injections each of 10 mg, over 80% of the patient's pain was relieved. The slow time course of pain relief suggests that the total cumulative dose is the relevant dose parameter.

Five minutes after the last phentolamine dose, 0.5 mg propranolol was given intravenously to counteract the tachycardia that was starting to become uncomfortable to the patient. This did not add appreciably to the analgesia already achieved with the α-adrenergic blockade. Propranolol was shown not to affect pain in patients. The patient's pain remained at this low level for about two hours, despite a plasma half-life of approximately 20 minutes for phentolamine. Pain gradually returned over the course of about three hours.

The LABSG procedure failed to afford long-term relief and the patient subsequently underwent a surgical lumbar sympathectomy. The patient had complete pain relief from this procedure and continues to be pain free as of 15 months post operatively.

Seventeen patients received both phentolamine and LABSG. The time of maximum relief of stimulus evoked pain correlated highly with the time at which there was maximum relief of stimulus-independent pain. All pain scores were converted to percent pain relief. The peak relief of stimulus independent pain for the LABSG compares favorably to the peak relief obtained from the phentolamine block. The range of peak relief for both procedures extended from near zero to 100%. Patients with less than 50% pain relief from both procedures were considered to have pain independent of SMP. There was a high correlation of the results of the two procedures ($r=0.78$). This shows that patients who experience substantive pain relief from LABSG also obtain substantive pain relief from phentolamine.

In five patients in whom the phentolamine block afforded more than 50% pain relief, the duration of pain relief lasted for several hours. The pain returned to within 75% of baseline within 2 to 7 hours.

Only one patient reported 45% maximum relief of pain with the LABSG but no relief with the phentolamine block.

There was a suggestion of greater specificity of results with phentolamine compared to LABSG. Of those patients who had 50% or greater pain relief following LABSG, the mean pain relief with phentolamine was 75% vs. 60% for the LABSG.

Side effects associated with the phentolamine administration other than the hemodynamic changes discussed above were minimal. The principal side effects observed were nasal stuffiness (12 patients), headache (3 patients), and dizziness (2 patients). The complications of the LABSG included mild headache, mild dizziness, back and neck pain from the needles, temporary paresis, and concurrent somatic block (thus negating LABSG) and requiring another procedure. When patients were asked which of the two sympathetic blocks they preferred, the patients chose the phentolamine block.

EXAMPLE 2

Topical Administration of Clonidine for Relief of SMP

A patient with a sciatic nerve injury was diagnosed as having SMP, based on lumbar sympathetic blockage. The patient had ongoing pain and intense hyperalgesia to both mechanical and cold stimuli in the painful zone. Clonidine was applied to the hyperalgesic zone transdermally via a 7.0 or 10.5 cm$^2$ patch (Catapres-TTS; Boehringer). These patches deliver 0.2 mg or 0.3 mg of clonidine/day for 7 days. A series of 6 patches were applied consecutively to different sites and each left in place for 2-10 days. Prior to, during, and post drug application, the heart rate and blood pressure were taken and sensory testing performed. Pain evoked by mechanical and cold stimuli was rated on a scale from 0-10.

Complete relief of hyperalgesia in the skin underlying the patch was achieved from each clonidine patch. There were no adverse side effects or changes in cardiovascular parameters. The skin surrounding the patch remained hyperalgesic even in the region adjacent to the edge of the patch. At each patch site, the pain evoked by deep pressure, light brushing and cooling stimuli was reduced within 24-36 hours and was completely abolished within 48 hours following patch application. This effect persisted for more than 24 hours after removal of the patch. A local anesthetic effect is unlikely since the patch did not alter (1) the detection threshold to mechanical stimuli in the patient, or (2) the detection or the pain threshold to mechanical stimuli in a normal subject.

EXAMPLE 3

Topical Administration of Clonidine Compared With Topical Administration of Clonidine Followed by Intradermal Injections of α-adrenergic Agonists.

Methods

Patient Selection and Control Subjects: Six normotensive patients with chronic ongoing pain and cutaneous hyperalgesia to mechanical and cooling stimuli following soft tissue or nerve trauma were examined. All patients had previously undergone sympathetic blocks (i.e., local anesthetic blockade of the appropriate sympathetic ganglia) to assess the involvement of the sympathetic nerves in their pain state. Additionally, in all but one patient (case 2) a systemic α-adrenergic block was performed via intravenous administration of phentolamine. Four of the six patients (cases 1-4) experienced 70-100% pain relief following the blocks and were considered to have SMP. The remaining two patients (cases 5, 6) were considered to have sympathetically-independent pain (SIP) since their pain was not affected by local anesthetic sympathetic ganglion block or the phentolamine block.

Five normal subjects were used as controls. One subject was used to investigate the effect of clonidine on normal skin (i.e., the top of the foot). The four remaining subjects were used to assess the effect of intradermal norepinephrine and phenylephrine in normal skin.

Topical Clonidine: Clonidine was administered to the hyperalgesic skin via a 7.0 or 10.5 cm$^2$ patch (Catapres-TTS$^R$-2 and TTS$^R$-3, Boehringer Ingelheim). These patches deliver a systemic does of 0.2 mg and 0.3 mg respectively of clonidine/day (i.e., 30 μg/cm$^2$/day) for a maximum of 7 days. A series of 2-7 patches were applied consecutively to different sites within the hyperalgesic zone. Each patch was left in place for 2-10 days within this affected zone. Prior to, during and immediately after drug application, the following parameters were monitored: heart rate, blood pressure, ongoing pain and pain to mechanical and cold stimuli.

Sensory Testing: To assess the local and systemic effects of clonidine, the following measures were used before application of the patch and immediately after removal of the patch: 1) Ongoing pain: stimulus-independent pain was assessed on a visual analog scale (VAS). The scale consisted of a 100 mm line where "no pain" and "most intense pain" were indicated on the left and right ends of the scale respectively. 2) Hyperalgesia to mechanical and cooling stimuli: Pain evoked by mechanical and cold stimuli was rated verbally on a scale from 0 ("no pain") to 10 ("most intense pain"). The mechanical stimuli included innocuous brushing with a camel's hair brush and innocuous pressure from the 206 g weight of a 13 mm diameter (i.e., 2N) brass probe. Pain thresholds to mechanical stimuli were determined in the area within and surrounding the patch sites using calibrated von Frey filaments. The cooling stimulus consisted of small drops of acetone lightly placed onto the patient's skin. Patients with SMP typically find that the 1°–2° C. decrease in temperature induced by such a stimulus is painful. 3) Tactile sensibility: To rule out local anesthetic effects, the detection (touch) thresholds were determined in the area within the surrounding selected patch sites using calibrated von Frey filaments. In addition, the patient's ability to distinguish the blunt from the sharp ends of a pin was also assessed. The patients were instructed to close their eyes during the hyperalgesia and von Frey threshold testing procedures.

Effects of Intradermal Norepinephrine and Phenylephrine: In two patients, intradermal injections of the non-specific α-adrenergic agonist norepinephrine (5 µg in 10 µl normal saline) or the α-adrenergic agonist phenylephrine (10 µg in 10 µl normal saline) were made at a patch site immediately after removing the patch. Norepinephrine and phenylephrine injections were also made at control sites on the patients' normal limb and into the normal skin of 4 healthy control subjects. Similar injection sites were chosen for the control subjects and patients. All injection were made in a single-blinded fashion. The patients and control subjects were instructed to rate the magnitude of any evoked pain and resultant hyperalgesia on a verbal scale from 0 to 10.

Results

The results of the clonidine applications in the control subject and six patient cases are summarized in Table 1. The first patient was studied extensively and is presented in detail as an illustrative example.

TABLE I

Summary of Individual Case Results

| | Case Number | | | | | |
|---|---|---|---|---|---|---|
| | 1 SMP | 2 SMP | 3 SMP | 4 SMP | 5 SIP | 6 SIP |
| Age/Sex: | 30/F | 45/F | 35/M | 52/F | 52/M | 42/F |
| Duration of Symptoms (Years): | 3 | 1.5 | 18 | 2 | 7 | 0.5 |
| Extremity Affected: | lower | lower | lower | face | upper | lower |
| Mechanical Hyperalgesia: | | | | | | |
| pre-clonidine | + | + | + | + | + | + |
| post-clonidine | − | − | nt | − | + | + |
| Touch Detection Threshold: | | | | | | |
| pre-clonidine (bars) | 4 | 1 | 1.5 | 0.5 | 1 | 2 |
| post-clonidine (bars) | 4 | 1 | 1.5 | 0.5 | 1 | 2 |

SMP = sympathetically maintained pain
SIP = sympathetically independent pain
+ = present, − = absent, nt = not tested Case 1:

The patient was a 30 year old, normotensive, white female who sustained an injury to the sciatic nerve from hip replacement surgery three years prior to entering the study. Subsequently, the patient developed continuous pain and hyperalgesia in the antero-lateral aspect of her left leg from the knee to the foot. Thermography revealed that most of this area was 1°–2° C. colder than corresponding parts of the contralateral leg. Within the affected region, the patient experienced intense ongoing pain and was exquisitely sensitive to mechanical stimuli. Mild mechanical stimuli (e.g., light brushing or pressure) evoked severe pain. Cooling stimuli (e.g., acetone) were not detected when applied to some parts of the affected area and were painful when applied to other parts. The results of local anesthetic sympathetic ganglion blocks and i.v. phentolamine blocks confirmed that her ongoing pain and hyperalgesia were sympathetically maintained.

This patient received a series of 7 clonidine patches. The patch was applied for 36 hours to an area of skin which had previously been hyperalgesic to brushing, pressure and cooling stimuli. After removal of the patch, mechanical (brush, pressure) and cooling (a drop of acetone) stimuli applied to this region were detected but were not painful, although these stimuli still elicited pain when applied to the adjacent skin. The mechanical detection thresholds inside and outside the patch site were identical and were similar to the contralateral leg. Within the patch site, the pain threshold to von Frey filaments approximated the patient's 'normal' pain threshold at a corresponding contralateral site and far exceeded the mechanical detection threshold. The ability to distinguish sharp from blunt stimuli were not affected at this site after the patch was removed. Outside the patch site, the pain threshold was low and approached the detection threshold. The patient's ratings of her stimulus-independent pain were not affected by the patch.

Although the patient was pleased with the relief achieved from the patches, treatment was discontinued when the patches started to produce skin irritations. Six months following the termination of the clonidine trial, she underwent a lumbar sympathectomy that completely eliminated her pain and hyperalgesia.

Extent of Pain and Hyperalgesia Relief By Topical Clonidine

A summary of the effect of four of the clonidine patches in which quantitative sensory testing was performed for case #1 is shown in FIG. 2. Each clonidine patch greatly reduced and, in many cases, completely eliminated the patient's hyperalgesia to mechanical stimuli. A confounding local anesthetic effect did not occur since detection thresholds were unchanged. The time course of the effect of each patch was not evaluated quantitatively. However, the patient did note a reduction of her mechanical hyperalgesia within 36–48 hours after the patch was applied to the skin. After removing a patch, hyperalgesia was still absent for at least 12 hours. Typically, the patient's hyperalgesia returned within less than a week of the patch application.

The three remaining patients diagnosed as having SMP achieved relief of their hyperalgesia following topical application of clonidine without any accompanying change in touch detection threshold (see Table I; cases 2-4). The original zone of hyperalgesia in two of these patients (cases 2,3) encompassed greater than half of the lower extremity. For these patients, topical clonidine only eliminated hyperalgesia at or near the site of drug application and did not alter stimulus-evoked pain outside these sites. Furthermore, these patients did not report any reduction in their overall level of stimulus-independent pain. In case #4, the zone of pain and hyperalgesia radiated laterally from a small region above the vermillion border in the maxillary nerve distribution. Following clonidine application to the upper lip, complete relief of hyperalgesia was obtained throughout the entire affected zone. The patient's ongoing pain was reduced by 50–75% and was confined to a very small region above the lip.

One of the patients diagnosed as having SIP (see Table I; case 5) had pain and hyperalgesia in the median nerve distribution of the left hand. Neither the patient's hyperalgesia nor ongoing pain were improved by application of clonidine to the palmar aspect of the hand. The second patient diagnosed as having SIP (case 6) had pain and hyperalgesia in the foot. The clonidine patches were applied to the dorsum of the foot and resulted in only a slight reduction (by approximately 35%) in both ongoing pain and in the mechanical hyperalgesia to brush stimuli. The hyperalgesia to cold stimuli was not affected by the clonidine patches.

Side Effects

The side effects from these clonidine patches were minor. The patients occasionally complained of feeling sleepy, thirsty and/or of having dry eyes. Following some of the patch applications, an erythematous rash was observed surrounding the patch site. This became a problem in two patients (cases 1, 4) and further treatment had to be discontinued despite good hyperalgesia relief. No appreciable alteration in the blood pressure or heart rate was apparent in any of the patients.

Sensory Effects of Topical Clonidine in Normal Skin

To exclude further local anesthetic effects of clonidine, a clonidine patch was applied to the top of a normal subject's foot and sensory testing was performed prior to and 40 hours after the patch application. Neither the pain nor detection threshold to von Frey filaments were affected in this subject. Mechanical and cooling stimuli were detected but were not painful before or after the clonidine had been applied.

Effect of Norepinephrine and Phenylephrine

To test the hypothesis that clonidine acts peripherally via reduction of norepinephrine release, an intradermal injection of norepinephrine (5 $\mu$g in 10 $\mu$l saline) was made at a previously hyperalgesic site that had been treated effectively with clonidine (case 1). Following removal of the clonidine patch and just prior to the injection, lightly brushing the skin at this site was only mildly hyperalgesic (rated 1 out of 10) whereas brushing the untreated skin evoked a pain sensation rated as 4 out of 10. The norepinephrine injection evoked an intense, burning pain sensation that subsided after four minutes. Twenty-five minutes after the injection, the patient's mechanical hyperalgesia at the patch site was rekindled and was rated as 3.5 out of 10. Injection of norepinephrine into the normal limb of this patient and the normal limb of another SMP patient (case 4), also evoked intense pain, but did not result in hyperalgesia. In contrast, intradermal injection of norepinephrine into the leg of four control subjects evoked a mild, short lasting pain and no hyperalgesia.

Since topical application of an $\alpha_2$-adrenergic agonist relieved hyperalgesia and a non-specific agonist rekindled hyperalgesia, it was hypothesized that $\alpha_1$-adrenergic receptors play an important role in SMP. To test this hypothesis directly the specific $\alpha_1$-adrenergic agonist phenylephrine was injected intradermally (10 $\mu$g in 10 $\mu$l saline) at a clonidine patch site and a normal site (volar forearm) in a patient with SMP (case #4) following 3 days of clonidine treatment. This patient's pain and hyperalgesia, which was localized to a small region of the face, was relieved by clonidine. Injection of phenylephrine at the clonidine patch site evoked intense stinging pain that subsided approximately 3 minutes after the injection. Approximately 25 minutes after the injection, the patient's hyperalgesia to mechanical and cooling stimuli returned. At this time, her ongoing level of pain also increased substantially. Injection of phenylephrine at the control site in this patient evoked moderate pain of shorter duration. Only brief, mild pain sensations and no hyperalgesia were evoked by the phenylephrine injections into the control subjects.

In summary, topical application of clonidine significantly reduced mechanical and cold hyperalgesia at the site of drug administration in patients with SMP. The decrease in hyperalgesia was not due to a local anesthetic effect since touch detection thresholds were not altered by the clonidine treatment in the patients and in the control subject. There was no change in the hyperalgesia outside the area of drug application in patients with a large zone of hyperalgesia. In addition, the ongoing, stimulus-independent pain was not affected by the clonidine patches in these patient. Clonidine had little effect on pain or hyperalgesia in the patients whose pain was independent of the sympathetics (cases 5 and 6). Local administration of adrenergic agonists into the affected skin in patients with SMP evoked unusually sustained, intense pain compared to the pain evoked in normal subjects. These observations indicate an important role of peripheral $\alpha_1$-adrenergic receptors in SMP.

Based on the above examples, it is clear that any $\alpha$-adrenergic antagonist, $\alpha$-1-adrenergic antagonist, $\alpha$2 adrenergic agonist, or other drug that depletes sympathetic norepinephrine, for example, bretylium, reserpine, phenoxybenzamine, or guanethidine, will relieve SMP using the method according to the present invention. Further, due to the number of side-effects and short effective half-lives associated with these compounds, topical administration of these compounds is preferred.

Modifications and variations of the compositions and methods of use thereof of the present invention will be obvious to those skilled in the art from the foregoing detailed description. Such modifications and variations are intended to come within the scope of the appended claims.

I claim:

1. A method of treating sympathetically maintained pain consisting of
   identifying patients with sympathetically maintained pain originating at a peripheral site and
   locally administering to the patient at the site of the sympathetically maintained pain an effective amount of an $\alpha$-2-adrenergic agonist to cause measurable pain relief.

2. The method of claim 1 wherein the drug is administered in a pharmaceutically acceptable carrier for topical application selected from the group consisting of a lotion, ointment, solution, and transdermal patch.

3. The method of claim 1 wherein the drug is clonidine.

4. The method of treatment of claim 3 wherein the drug is clonidine administered transdermally through a patch.

5. The method of claim 4 wherein the patch delivers from 0.2 to 0.3 mg of clonidine per day for seven days.

* * * * *